United States Patent [19]

Corey

[11] Patent Number: 4,943,635
[45] Date of Patent: Jul. 24, 1990

[54] ENANTIOSELECTIVE REDUCTION OF KETONES

[75] Inventor: Elias J. Corey, Cambridge, Mass.

[73] Assignee: President & Fellows of Harvard College, Cambridge, Mass.

[21] Appl. No.: 224,697

[22] Filed: Jul. 29, 1988

Related U.S. Application Data

[63] Continuation-in-part of Ser. No. 90,196, Aug. 27, 1987, abandoned.

[51] Int. Cl.$^5$ .......................... C07B 53/00; C07F 5/02
[52] U.S. Cl. ...................................... 546/13; 548/405; 548/950; 558/289; 568/881
[58] Field of Search ................ 558/289; 548/405, 950; 546/13

[56] References Cited

U.S. PATENT DOCUMENTS 4,749,809  6/1988  Yoneyoshi et al. ................. 558/384
4,751,017  6/1988  Wachtler ............................ 546/13

FOREIGN PATENT DOCUMENTS 146786  of 1982  Japan .
 10024  of 1987  Japan .
WO84/3885  6/1984  PCT Int'l Appl. .

OTHER PUBLICATIONS

E. J. Corey et al, J. Org. Chem. 53, 2861 (1988).
J. W. Apsimon et al., Tetrahedron, 42 (19), 5157–5254 (1986) (excerpts).
A. Hirao et al., J.C.S. Chem. Commun., 1981, 315–317.
S. Hsuno et al., J.C.S. Chem. Commun., 1983, 469–470.
S. Husno et al., J.C.S. Perkin Trans. I, 1983, 1673–1676.
S. Hsuno et al., J. Org. Chem., 1984, 49, 555–557.
S. Hsuno et al., J.C.S. Perkin Trans. I, 1984, 2887–2893.
S. Hsuno et al., Bull. Chem. Soc. Japan, 58, 1669–1673 (1985).
S. Hsuno et al., J.C.S. Perkin Trans. I, 1985, 2039–2044.
S. Hsuno et al., J.C.S. Perkin Trans. I, 1985, 2615–2619.
S. Hsuno et al., Bull. Chem. Soc. Japan, 60, 395–6 (1987).
H. C. Brown et al., Organometallics, 1985, 4, 816–821.
H. R. Snyder et al., J. Am. Chem. Soc., 60, 105–111 (1938).
P. A. McCusker et al., J. Am. Chem. Soc., 79, 5179–5181 (1957).
R. H. Cragg et al., J. Organomet. Chem., 154 (1978), C3–C5.
R. H. Cragg et al., J.C.S. Dalton Trans, 1975, 93–95.
J. Biolawski et al., Synth. React. Inorg. Met. Org. Chem., 10(5), 479–489 (1980).
K. Neidenzu et al., Chem. Ber. 105, 2258–2263 (1972).
H. C. Brown et al., J. Org. Chem., 1986, 51, 4526–4530.
C. J. W. Brooks et al., J. Chromatog. Sci., 9, 18–24 (1971).
C. F. Poole et al., J. Chromatography, 186 (1979), 307–316.
N. E. Miller, Inorg. Chem., 13, 1459–1467 (1974).
N. E. Miller, J. Am. Chem. Soc., 92, 4564–4571 (1970).
M. F. Grundon et al., Tet. Lett., 4, 295–296 (1976).
M. F. Grundon et al., J.C.S. Perkin Trans. I, 1981, 231–235.
In Kwon Youn et al., Tet. Lett., 29, 4453–4456 (1988).
E. J. Corey et al., Tet. Lett., 29, 3201–3204 (1988).
E. J. Corey et al., J. Am. Chem. Soc., 1988, 110, 3672–3673.
E. J. Corey et al., J. Am. Chem. Soc., 1987, 109, 7925–7926.
E. J. Corey et al., J. Am. Chem. Soc., 1987, 109, 5551–5553.

Primary Examiner—Mark L. Berch
Attorney, Agent, or Firm—Derek P. Freyberg

[57]  ABSTRACT

Chiral 1,3,2-oxazaborolidines and tetrahydro-1,3,2-oxazaborines are effective catalysts for the borane reduction of prochiral ketones to optically active alcohols.

30 Claims, No Drawings

ENANTIOSELECTIVE REDUCTION OF KETONES

STATEMENT OF GOVERNMENT INTEREST

This invention was made with Government support, including National Science Foundation Research Grant No. CHE84-13444. The Government has certain rights in the invention.

CROSS-REFERENCE TO RELATED APPLICATION

This application is a continuation-in-part of my copending and commonly assigned application Ser. No. 07/090,196, filed Aug. 27, 1987, ABN which is incorporated herein by reference in its entirety.

BACKGROUND OF THE INVENTION

1. Field of the Invention

This invention relates to the enantioselective borane reduction of prochiral ketones and to certain borane-containing compounds useful as catalysts for that purpose.

2. Prior Art

Recently there have been a number of reports describing research on the enantioselective reduction of prochiral ketones by a wide variety of reagents made by mixing aluminum or boron hydrides and various chiral diols or aminoalcohols. See, for example, J. W. ApSimon et al., Tetrahedron, 42, 5157–254 (1986). Among the most interesting enantioselective prochiral ketone reductions have been those reported by S. Itsuno and co-workers which employ borane in tetrahydrofuran (THF) and a chiral β-amino alcohol, (S)-2-amino-3-methyl-1,1-diphenylbutan-1-ol and the corresponding derivative from (S)-leucine thus far being the most effective (ca. 95% e.e. of (R)-1-phenylethanol from acetophenone). See, for example, J. Chem. Soc. Chem. Commun., 315–7 (1981); J. Chem. Soc. Chem. Commun., 469–70 (1983); J. Org. Chem., 49, 555–7 (1984); J. Chem. Soc. Perkin Trans. I, 2039–44 (1985); J. Chem. Soc. Perkin Trans. I, 2615–9 (1985); Bull. Chem. Soc. Japan, 60, 395–6 (1987). The disclosures of these and other documents referred to in the specification of this application are incorporated herein by reference.

SUMMARY OF THE INVENTION

I have discovered that chiral 1,3,2-oxazaborolidines and tetrahydro-1,3,2-oxazaborines are catalytic for the borane reduction of a prochiral ketone to an optically active alcohol, by which I mean that a prochiral ketone may be reduced to an optically active alcohol in the presence of a substantially sub-stoichiometric amount of the oxazaborolidine or oxazaborine.

In a first aspect, this invention relates to a process for the reduction of a prochiral ketone to an optically active alcohol which comprises treating the prochiral ketone with borane in the presence of a catalytically effective amount of either:

(a) a chiral 1,3,2-oxazaborolidine of the formula:

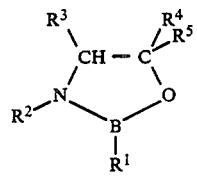

in which:
$R^1$ is hydrogen, lower alkyl, or aralkyl;
$R^2$ is hydrogen, methyl, or ethyl;
$R^3$ is alkyl, aryl, or aralkyl; or $R^2$ and $R^3$, taken together with that part of the oxazaborolidine ring to which they are attached, form a 4-, 5-, or 6-membered ring; and
$R^4$ and $R^5$ are independently alkyl, aryl, or aralkyl; or $R^2$ and $R^4$, taken together with that part of the oxazaborolidine ring to which they are attached, form a 5- or 6-membered ring and $R^5$ is hydrogen; or $R^2$, $R^3$, and $R^4$, taken together with that part of the oxazaborolidine ring to which they are attached, form two 5-membered rings, cis-fused at the CH-$R^3$ bond, or (b) a chiral tetrahydro-1,3,2-oxazaborine of the formula:

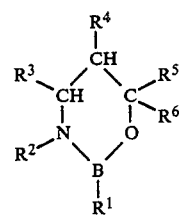

in which:
$R^1$ is hydrogen, lower alkyl, or aralkyl;
$R^2$ is hydrogen, methyl, or ethyl;
$R^3$ is alkyl, aryl, or aralkyl; or $R^2$ and $R^3$, taken together with that part of the oxazaborine ring to which they are attached, form a 4-, 5-, or 6-membered ring;
$R^4$ is hydrogen, alkyl, or aryl; or $R^2$ and $R^4$, taken together with that part of the oxazaborine ring to which they are attached, form a 5- or 6-membered ring; and
$R^5$ and $R^6$ are independently alkyl, aryl, or aralkyl; or $R^2$ and $R^5$, taken together with that part of the oxazaborine ring to which they are attached, form a 6-membered ring and $R^6$ is hydrogen.

In a second aspect, this invention relates to a catalyst for the borane reduction of a prochiral ketone to an optically active alcohol which comprises either:

(a) a chiral 1,3,2-oxazaborolidine of formula I in which either:

(1) $R^1$ is lower alkyl or aralkyl; and $R^2$, $R^3$, $R^4$ and $R^5$ are as first defined for formula I, or (2) $R^1$, $R^4$ and $R^5$ are as first defined for formula I; and $R^2$ and $R^3$, taken together with that part of the oxazaborolidine ring to which they are attached, form a 4-, 5-, or 6-membered ring, or (3) $R^1$ and $R^3$ are as first defined for formula I; and $R^1$ and $R^4$, taken together with that part of the oxazaborolidine ring to which they are attached, form a 5- or 6-membered ring and $R^5$ is hydrogen, or (4) $R^1$ and $R^5$ are as first defined for formula I; and $R^2$, $R^3$, and $R^4$, taken together with that part of the oxazaborolidine ring to which they are attached, form two 5-membered rings, cis-fused at the CH-$R^3$ bond, or (b) a chiral tetrahydro-1,3,2-oxazaborine of formula II in which $R^1$, $R^2$, $R^3$, $R^4$, $R^5$ and $R^6$ are as first defined for formula II.

DETAILED DESCRIPTION OF THE INVENTION

Definitions

As used herein, unless the context otherwise requires:

"alkyl" means a branched, unbranched, or cyclic saturated hydrocarbon group containing from one to eight carbon atoms. Examples are methyl, ethyl, 2-propyl, 1-butyl, neopentyl (2,2-dimethyl-1propyl), 1-hexyl, cyclohexyl, cyclopentylmethyl, tert-octyl (1,1,3,3-tetramethyl-1-butyl), and the like;

"lower alkyl" means a branched or unbranched saturated hydrocarbon chain containing from one to four carbon atoms. Examples are methyl, ethyl, 2-propyl, 1-butyl, and the like;

"bulkyl alkyl" means a branched or cyclic saturated hydrocarbon group containing from three to either carbon atoms. Examples are 2-propyl, tert-butyl (1,1-dimethylethyl), neopentyl (2,2-dimethyl-1-propyl), cyclohexyl, cyclopentylmethyl, tert-octyl (1,1,3,3-tetramethyl-1-butyl), and the like;

"aryl" means either phenyl or $\beta$-naphthyl, each optionally substituted with one to three substituents selected from lower alkyl, lower alkyloxy, and halogens.

"aralkyl" means $\omega$-aryl-(lower alkyl), where aryl and lower alkyl are as described above.

a "catalytically effective" amount of a material is that sub-stoichiometric amount which is sufficient to facilitate the conversion of a desired reactant to product(s).

"enantiomeric excess", or e.e., is the excess of one of two enantiomers over the other, usually expressed as a percentage, i.e. a 90% e.e. reflects the presence of 95% of one enantiomer and 5% of the other in the material in question.

a "prochiral ketone", denoted by $R_SR_LCO$, is a ketone in which $R_S$ and $R_L$ are non-identical, so that the secondary alcohol reduction product $R_SR_LCHOH$ has a chiral center at the alcohol carbon.

The Reduction Process

The reduction process of the invention comprises treating a prochiral ketone, which it is desired to reduce to an optically active alcohol, with borane in the presence of a catalytically effective amount of a catalyst which is either a chiral oxazaborolidine of formula I or a chiral oxazaborine of formula II.

Without any limitation being implied by the following, the process is considered to proceed in the following manner:

(1) A molecule of borane coordinates to the oxazaborolidine/oxazaborine (the catalyst) at the nitrogen, forming a catalyst-borane complex;

(2) The prochiral ketone, denoted by $R_SR_LCO$, $R_S$ and $R_L$ being relatively smaller and larger groups, coordinates via its carbonyl oxygen to the ring boron atom of the complex in an orientation determined by steric interaction between the prochiral ketone and the complex;

(3) A proton transfers from the coordinated borane to the prochiral ketone, forming an optically active alkoxide, still coordinated to the ring boron;

(4) The coordinated alkoxide reacts with additional borane to form a non-coordinated optically active alkoxyborane (or dialkoxyborane) and regenerate the catalyst-borane complex; and (5) The alkoxyborane is hydrolyzed to the optically active alcohol product.

The above-described mechanism is illustrated, for (S)-5,5-diphenyl-3,4-propano-1,3,2-oxazaborolidine (the oxazaborolidine formed from the reaction of borane with (S)-(−)-$\alpha,\alpha$-diphenyl-2-pyrrolidinemethanol) as the catalyst in the following manner:

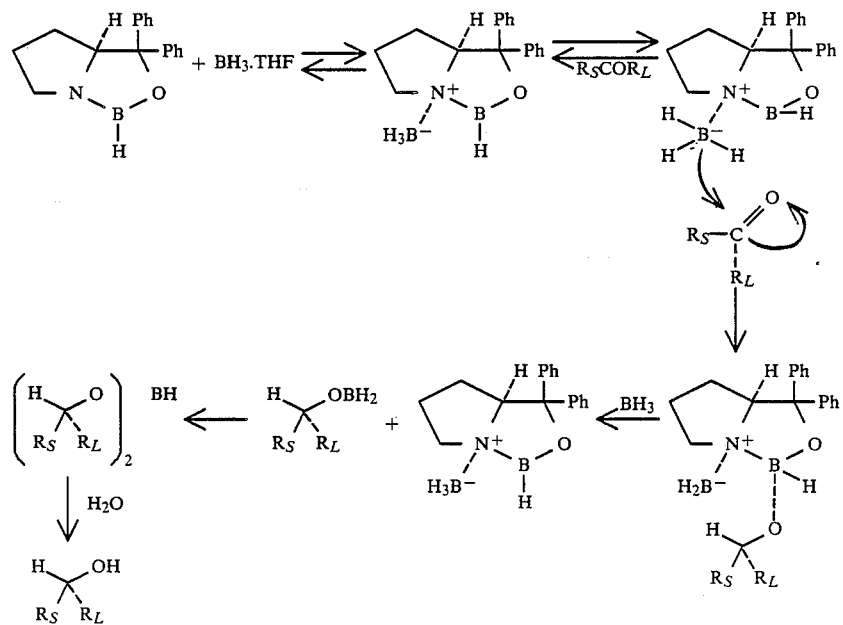

As illustrated by the reaction scheme above, the stereochemistry of the product optically active alcohol (the enantioselectivity of the reduction) is predictable on mechanistic grounds from the three-dimensional properties of the catalyst molecule and the prochiral ketone. The prochiral ktone preferentially coodinates to the catalyst-borane complex such that $R_L$ is trans to the ring boron atom of the complex, thereby determining the face of the prochiral ketone to which a hydrogen atom is transferred. Thus the reduction of a prochiral ketone $R_S R_L CO$ with (S)-5,5-diphenyl-3,4-propano-1,3,2-oxazaborolidine results in an alcohol $R_S R_L CHOH$ of (R)-configuration (if $R_L$ is considered senior in Sequence Rule terms to $R_S$), the (S)-configuration of 2-chloro-1-phenylethanol in Tables I and II being dictated by strict application of the Sequence Rule in this case making $R_S$ (the —CH₂Cl group) senior to $R_L$ (the phenyl group). Conversely, (R)-5,5-diphenyl-3,4-propano-1,3,2-oxazaborolidine will produce (S)-alcohols (cf. Table II, note g); and one of ordinary skill in the art will experience no difficulty, having regard to his own knowledge and this disclosure, in determining a suitable catalyst configuration for a desired optically active alcohol product configuration.

The prochiral ketone, $R_S R_L CO$, may be any prochiral ketone in which $R_S$ and $R_L$ are inert to borane. That is, $R_S$ and $R_L$ may independently be any organic radicals, e.g. alkyl, aryl, or aralkyl (the term "alkyl" is used here in its broadest sense as meaning non-aromatic hydrocarbyl, and includes e.g. alkenyl, and the term "aryl" means aromatic hydrocarbyl, and includes e.g. phenyl and naphthyl), and they may be taken together to form a ring system so that $R_S R_L CO$ is cyclic (e.g. tetralone). $R_S$ and $R_L$ may independently substituted with any borane-inert substituents (as, e.g., alkyl, alkoxy, halo, etc.). The extent of enantioselectivity of the reduction process of the invention will depend to some extent on the relative sizes of $R_S$ and $R_L$, a greater difference in size implying a greater enantiomeric excess, other conditions being equal.

Suitable prochiral ketones for the process include for example dialkyl ketones such as t-butyl methyl ketone and methyl cyclohexyl ketone, alkyl aryl ketones such as acetophenone, propiophenone, chloroacetophenone, and 2-acetyl-6-methoxynaphthalene, cyclic ketones such as α-tetralone and 2-bromo-2-cyclohexene-1-one, etc. Prochiral ketones which are already chiral, for example the prostaglandin intermediates 3α,5α-dihydroxy-2β-(3-oxo-trans-1-octenyl)-1α-cyclopentaneacetic acid γ-lactone ["Corey lactone"] and 3α,5α-dihydroxy-2β-(3-oxo-4-phenoxy-trans-1-butenyl)-1α-cyclopentaneacetic acid γ-lactone, which contain a keto function in a side-chain, and the like, as exemplified later in the specification of this application, are also suitable.

The alcohols which are products of this process may be of interest as products per se, as chiral reagents (e.g. 1-phenylethanol), or as intermediates in further chemical synthesis (e.g. optically active 1-(6-methoxy-2-naphthyl)ethanol, an intermediate for naproxen, and the optically active prostaglandin intermediate lactone in the second last line of table II).

The process takes place in a suitable solvent, by which is meant any solvent capable of sufficient dissolution of the catalyst, ketone, and resulting alkoxyborane, and inert to borane. Suitable solvents are aprotic, non-basic solvents such as ethers (e.g. tetrahydrofuran, tetrahydropyran, diethyl ether, etc.) and aromatic hydrocarbons (e.g. benzene, toluene, etc.), which may also contain aliphatic hydrocarbons, halogenated hydrocarbons, and other borane-stable solvents, as desired. Preferred solvents are ethers, especially tetrahydrofuran.

Typically, the catalyst is dissolved in a solution of borane in a suitable solvent, e.g. in 1M BH₃.THF, which is readily commercially available, ethanedithiol di-t-butyl thioether bis(borane) in toluene, etc. at a temperature between about 0° and 80° C., generally at about ambient temperature (25° C.), and a solution of the prochiral ketone in the same or another suitable solvent is added, again at a temperature between about 0° and 80° C., typically at ambient temperature. Alternatively, the catalyst and prochiral ketone are dissolved in a suitable solvent, and a solution of borane added. The reaction proceeds rapidly, typically within a few minutes, e.g. 1-10 minutes, to produce a reaction mixture containing the alkoxyborane/dialkoxyborane. The reaction mixture is then treated with acid, preferably an alcoholic acid, e.g. 2M hydrogen chloride in methanol, to generate the optically active alcohol product and volatile trimethyl borate. The product may be isolated by any conventional means, typically by evaporation of the solvent and volatile trimethyl borate, addition of solvent (e.g. diethyl ether and a small amount of water), separation and evaporation of the organic layer to provide the optically active alcohol and basification of the aqueous layer and extraction to allow recovery of the aminoalcohol catalyst precursor, as described in more detail below, and purification by conventional means such as chromatography, distillation, etc.

The molar ratio of borane to reactant prochiral ketone may be from 0.5:1 (the theoretical requirement of borane) to 2:1 or greater. Preferably, however, the borane/prochiral ketone ratio should be near the lower end of that range, e.g. 0.5:1 to 1:1, e.g. 0.6:1, as excessive amounts of borane may lead to uncatalyzed (and hence non-enantioselective) reduction of the prochiral ketone, lowering the e.e. of the product alcohol.

The oxazaborolidine/oxazaborine catalyst is employed in a catalytically effective amount, as defined previously. For a material to be considered a catalyst, a catalytically effective amount will be substantially sub-stoichiometric with respect to the reactant prochiral ketone, i.e. it will be less than 0.5, preferably less than 0.25, more preferably no greater than 0.1 moles/mole of prochiral ketone. Yet lower amounts of catalyst, e.g. 0.01 to 0.05 moles/mole of prochiral ketone, may be employed and are functional; however, too little catalyst may (as with the presence of excessive borane) lead to uncatalyzed (and hence non-enantioselective) reduction of the prochiral ketone, lowering the e.e. of the product alcohol.

If desired, additional borane and prochiral ketone may be added to the reaction mixture and allowed to react further before the hydrolysis step, and this borane-prochiral ketone addition and reaction may be performed more than once before the final reaction mixture is hydrolyzed. This technique effective decreases the catalyst/prochiral ketone ratio, in a fashion which still provides for adequate enantioselectivity of the reduction process.

Further, the catalyst may be "regenerated" following the hydrolysis. Alcoholysis of the reaction mixture to yield the optically active alcohol product decomposes the catalyst, affording the ciral aminoalcohol which is the catalyst precursor (see the Preparation of the Catalyst section of this application), e.g. as the hydrochloride salt. The chiral aminoalcohol may be isolated by conventional means from the reaction mixture, especially from the aqueous layer remaining after acid alcoholysis of the reaction mixture, addition of organic solvent, and removal of the product optically active alcohol in the organic layer. That aqueous layer, if suitably acidified, will contain the chiral aminoalcohol catalyst precursor in the form of an acid addition salt, which may be isolated and purified by conventional means (e.g. precipitation, redissolution in base, extraction of the aminoalcohol into organic solvent, and evaporation of the solvent) and the catalyst regenerated by reaction of the aminoalcohol with borane or a (lower alkyl)boronic acid in the manner described below.

The techniques of borane reduction per se being generally well-known, as exemplified for example by the references in the Background to the Invention section of this application, it is considered that one of ordinary skill in the art, having regard to his own knowledge and this disclosure, should have no difficulty in choosing suitable quantities of borane and catalyst, and suitable reaction and work-up conditions, for carrying out the reduction process of the invention.

The Catalyst

The catalyst useful in the reduction process of this invention is either:

(a) a chiral 1,3,2-oxazaborolidine of the formula:

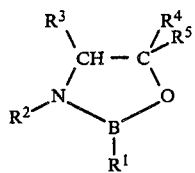

(I)

in which:

$R^1$ is hydrogen, lower alkyl, or aralkyl;

$R^2$ is hydrogen, methyl, or ethyl;

$R^3$ is alkyl, aryl, or aralkyl; or $R^2$ and $R^3$, taken together with that part of the oxazaborolidine ring to which they are attached, form a 4-, 5-, or 6-membered ring; and $R^4$ and $R^5$ are independently alkyl, aryl, or aralkyl; or $R^2$ and $R^4$; taken together with that part of the oxazaborolidine ring to which they are attached, form a 5- or 6-membered ring and $R^5$ is hydrogen, or $R^2$, $R^3$, and $R^4$, taken together with that part of the oxazaborolidine ring to which they are attached, form two 5-membered rings, cis-fused at the CH—$R^3$ bond, or (b) a chiral tetrahydro-1,3,2-oxazaborine of the formula:

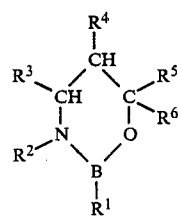

(II)

in which:

$R^1$ is hydrogen, lower alkyl, or aralkyl;

$R^2$ is hydrogen, methyl, or ethyl;

$R^3$ is alkyl, aryl, or aralkyl; or $R^2$ and $R^3$, taken together with that part of the oxazaborine ring to which are attached, form a 4-, 5-, or 6-membered ring;

$R^4$ is hydrogen, alkyl, or aryl; or $R^2$ and $R^4$, taken together with that part of the oxazaborine ring to which they are attached, form a 5- or 6-membered ring; and $R^5$ and $R^6$ are independently alkyl, aryl, or aralkyl; or $R^2$ and $R^5$, taken together with that part of the oxazaborine ring to which they are attached, form a 6-membered ring and $R^6$ is hydrogen.

Certain of the oxazaborolidones of formula I are known per se, and are known for the stoichiometric reduction of prochiral ketones and the catalytic reduction of prochiral ketone O-alkyloximes; however they are not believed to be known for the catalytic reduction of prochiral ketones.

Novel oxazaborolidines of formula I include those where either;

(1) $R^1$ is lower alkyl or aralkyl; and $R^2$, $R^3$, $R^4$ and $R^5$ are as first defined for formula I, or (2) $R^1$, $R^4$ and $R^5$ are as first defined for formula I; and $R^2$ and $R^3$, taken together with that part of the oxazaborolidine ring to which they are attached, form a 4-, 5-, or 6-membered ring, or (3) $R^1$ and $R^3$ are as first defined for formula I, and $R^2$ and $R^4$, taken together with that part of the oxazaborolidine ring to which they are attached, form a 5- or 6-membered ring and $R^5$ is hydrogen, or (4) $R^1$ and $R^5$ are as first defined for formula I; and $R^2$, $R^3$, and $R^4$, taken together with that part of the oxazaborolidine ring to which they are attached, form two 5-membered rings, cis-fused at the CH—$R^3$ bond.

Preferred oxazaborolidines of formula I are those in which one or (preferably) more than one of the following are true:

(1) $R^1$ is hydrogen, methyl, or ethyl; with $R^1$ is hydrogen being more preferred;

(2) $R^2$ forms part of a ring with $R^3$ or $R^4$, or is hydrogen;

(3) $R^3$ forms part of a ring with $R^2$, or is bulky alkyl, aryl, or aralkyl; or (4) $R^4$, if not forming part of a ring with $R^2$ (in which case $R^5$ is hydrogen), and $R^5$ are bulky alkyl, aryl, or aralkyl, and are more preferably the same (for ease of synthesis).

Particularly preferred oxazaborolidines of formula I are those in which:

(1) $R^1$ is hydrogen, methyl, or ethyl; with $R^1$ is hydrogen being more preferred;

(2) $R^2$ and $R^3$, taken together with that part of the oxazaborolidine ring to which they are attached, form a 4-, 5-, or 6-membered ring, more preferably a 4- or 5-membered ring, e.g. where $R^2$ and $R^3$ together form a 1,2-ethano, 1,3-propano, or 1,4-butano bridge, more preferably, a 1,2-ethano or 1,3-propano bridge; and (3) $R^4$ and $R^5$ are bulky alkyl, aryl, or aralkyl, and are more preferably the same (for ease of synthesis).

Exemplary of these particularly preferred chiral oxazaborolidines are: (S)-5,5-diphenyl-3,4-propano-1,3,2-oxazaborolidine and (S)-5,5-di(t-butyl)-3,4-ethano-1,3,2-oxazaborolidine (i.e. those oxazaborolidines formed from the reaction of borane with (S)-(−)-α,α-diphenyl-2-pyrrolidinemethanol and (S)-(−)-α,α-di(t-butyl)-2-azetidinemethanol), and the like.

Other particularly preferred oxazaborolidines of formula I are those in which:

(1) $R^1$ is hydrogen, methyl, or ethyl; with $R^1$ is hydrogen being more preferred;

(2) $R^2$ and $R^4$, taken together with that part of the oxazaborolidine ring to which they are attached, form a 5- or 6-membered ring, more preferably a 6-membered ring;

(3) $R^3$ is bulky alkyl, aryl, or aralkyl; and (4) $R^5$ is hydrogen.

Preferred oxazaborines of formula II are those in which one or (preferably) more than one of the following are true:
(1) $R^1$ is hydrogen, methyl, or ethyl; with $R^1$ is hydrogen being more preferred;
(2) $R^2$ forms part of a ring with $R^3$, $R^4$, or $R^5$, or is hydrogen;
(3) $R^3$ forms part of a ring with $R^2$, or is bulky alkyl, aryl, or aralkyl;
(4) $R^4$ forms part of a ring with $R^2$, or is hydrogen or lower alkyl, preferably hydrogen; or
(5) $R^5$, if not forming part of a ring with $R^2$ (in which case $R^6$ is hydrogen), and $R^6$ are bulky alkyl, aryl, or aralkyl, and are more preferably the same (for ease of synthesis).

Particularly preferred oxazaborines of formula II are those in which:
(1) $R^1$ is hydrogen, methyl, or ethyl; with $R^1$ is hydrogen being more preferred;
(2) $R^2$ and $R^3$, taken together with that part of the oxazaborine ring to which they are attached, form a 4-, 5-, or 6-membered ring, more preferably a 4- or 5-membered ring, e.g. where $R^2$ and $R^3$ together form a 1,2-ethano, 1,3-propano, or 1,4-butano bridge, more preferably, a 1,2-ethano or 1,3-propano bridge;
(3) $R^4$ is hydrogen or lower alkyl, preferably hydrogen; and
(4) $R^5$ and $R^6$ are bulky alkyl, aryl, or aralkyl, and are more preferably the same (for ease of synthesis).

Exemplary of these particularly preferred chiral oxazaborines are: (S)-2H,4H,5H,6H-6,6-diphenyl-3,4-propano-1,3,2-oxazaborine and (S)-2H,4H,5H,6H-3,4-butano-6,6-diphenyl-1,3,2-oxazaborine (i.e. those oxazaborines formed from the reaction of borane with (S)-β,β-diphenyl-2-pyrrolidineethanol, (S)-β,β-di(t-butyl)-2-piperidineethanol), and the like.

Preparation of the Catalyst

The oxazaborolidine or oxazaborine catalysts of this invention may be prepared by the reaction of an aminoalcohol (a β-aminoalcohol for the oxazaboroilidines or a δ-aminoalcohol for the oxazaborines) with:
(a) borane, if $R^1$ is to be hydrogen, or
(b) a (lower alkyl/aralkyl)boronic acid, if $R^1$ is to be lower alkyl or aralkyl.

The preparations may be by techniques generally known to the art for the preparation of already-known oxazaborolidines, such as by the techniques disclosed in the reference in the Background to the Invention section of this application, or by the techniques discussed below.

In the case where $R^1$ is hydrogen, the aminoalcohol is typically dissolved in a borane-containing solution, e.g. in an ether, such as $BH_3 \cdot THF$ (which is commercially available), or a solution of the aminoalcohol in a suitable solvent (such as the solvent for the borane, e.g. an ether such as THF, or an aromatic hydrocarbon, etc.) is added to a borane-containing solution, as before. The borane/aminoalcohol ratio is typically between about 2:1 and 5:1, usually about 2:1 to 3:1. The resulting reaction mixture is stirred at a temperature between about 0° C. and the reflux temperature of the solvent, preferably between ambient temperature and the reflux temperature of the solvent, e.g. at about 35° C., under an inert atmosphere (e.g. nitrogen, argon, etc.) at ambient or moderately superambient pressure, e.g. 1 to 3 bar, until the reaction is complete, typically for a time between about 1 and 72 hours, preferably 3 to 48 hours. The resulting oxazaborolidine/oxazaborine may be isolated and purified (if desired) by conventional means, such as evaporation of the solvent, typically under reduced pressure, for isolation and vacuum sublimation or Kugelrohr distillation of the catalyst for purification. The resulting catalysts, when pure, are typically stable colorless crystalline materials having definite melting points.

In the case where $R^1$ is lower alkyl or aralkyl, a solution of the aminoalcohol and the (lower alkyl/aralkyl)-boronic acid, $R^1B(OH)_2$, in a suitable solvent (e.g. an aromatic hydrocarbon, such as toluene) is heated under an inert atmosphere while removing the water produced by the reaction, e.g., the reaction mixture may be refluxed under an inert atmosphere using a Dean-Stark apparatus. The (lower/alkylaralkyl)boronic acid/aminoalcohol ratio is typically only slightly greater than stoichiometric, e.g. about 1.05:1 to 1.2:1, especially about 1.1:1. Isolation and purification of the resulting B-substituted oxazaborolidine/oxazaborine may be performed in the conventional manner, as exemplified above for the B-unsubstituted catalysts.

While the oxazaborolidine/oxazaborine catalysts of the invention are isolable, and may be isolated as described above, it is within the contemplation of the invention that they may be prepared in situ and used without isolation. Thus, for example, the solution resulting from the reaction of the aminoalcohol precursor and borane/(lower alkyl/aralkyl)boronic acid as described in the two preceding paragraphs may simply be used directly in the catalytic reduction process previously described, by addition of additional solvent (if necessary or desired), borane, and prochiral ketone, and treatment as described in the The Reduction Process section of the application above.

(Lower alkyl/aralkyl)boronic acids, such as n-butyl-boronic acid, 3-phenylpropylboronic acid, (S)-2-(6-methoxy-2-naphthyl)propylboronic acid, etc., may be prepared by methods known to the art. See, for example, H. C. Brown and T. E. Cole, Organometallics, 4, 816–21 (1985), which is incorporated herein by reference, and references cited therein, for the preparation of methylboronic acid. See also, for example, H. R. Synder, J. A. Kuck, and J. R. Johnson, J. Am. Chem. Soc., 60, 105 (1938), which is also incorporated herein by reference, for the preparation of methylboronic acid and other (lower alkyl)-boronic acids.

The chiral aminoalcohol precursors to the catalysts of the invention may be prepared by methods known to the art for the preparation of already-known aminoalcohols, such as by the techniques disclosed in the references in the Background to the Invention section of this application, or by the techniques discussed below.

Suitable chiral β-aminoalcohols are of the formula:

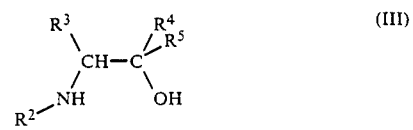

(III)

in which:
$R^2$ is hydrogen, methyl, or ethyl;
$R^3$ is alkyl, aryl, or aralkyl; or $R^2$ and $R^3$, taken together with that part of the alcohol to which they are attached, form a 4-, 5-, or 6-membered ring; and $R^4$ and $R^5$ are independently alkyl, aryl, or aralkyl; or $R^2$ and $R^4$, taken together with that part of the alcohol to which they are attached, form a 5- or 6-membered ring and $R^5$ is hydrogen, or $R^2$, $R^3$, and $R^4$, taken together with that part of the alcohol to which they are attached, form two 5-membered rings, cis-fused at the CH—$R^3$ bond.

Preferred β-aminoalcohols of formula III are those in which one or (preferably) more than one of the following are true:
(1) $R^2$ forms part of a ring with $R^3$ or $R^4$, or is hydrogen;
(2) $R^3$ forms part of a ring with $R^2$, or is bulky alkyl, aryl, or aralkyl; or
(3) $R^4$, if not forming part of a ring with $R^2$ (in which case $R^5$ is hydrogen), and $R^5$ are bulky alkyl, aryl, or aralkyl, and are more preferably the same (for ease of synthesis).

Particularly preferred β-aminoalcohols of formula III are those in which:
(1) $R^2$ and $R^3$, taken together with that part of the alcohol to which they are attached, form a 4-, 5- or 6-membered ring, more preferably a 4- or 5-membered ring; and
(3) $R^4$ and $R^5$ are bulky alkyl, aryl, or aralkyl, and are more preferably the same (for ease of synthesis).

Other particularly preferred β-aminoalcohols of formula III are those in which:
(1) $R^2$ and $R^4$, taken together with that part of the alcohol to which they are attached, form a 5- or 6-membered ring, more preferably a 6-membered ring;
(2) $R^3$ is bulky alkyl, aryl, or aralkyl; and
(4) $R^5$ is hydrogen.

In the case where $R^2$, $R^3$, and $R^4$, taken together with the part of the alcohol to which they are attached, form two 5-membered rings, cis-fused at the CH—$R^3$ bond, i.e. when the β-aminoalcohol is of the form:

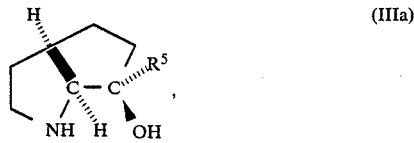

(IIIa)

$R^5$ is preferably bulky alkyl, aryl, or aralkyl, more preferably aryl; and the alcohol is prepared by the reaction of an N-protected cis-2-aza-bicyclo[3.3.0]octan-8-one with a Grignard reagent (as discussed below) or an aryllithium or similar reagent (as illustrated in the Examples), followed by resolution to afford the desired single isomer.

In the case where $R^4$ does not form part of a ring, $R^4$ and $R^5$ are preferably the same and the aminoalcohols may be most conveniently prepared by the reaction of an ester, typically a lower alkyl ester, of an α-aminoacid with a Grignard reagent of the form $R^4MgX$ (where X is halogen). Such a synthesis is known, for example, for the preparation of 2-amino-3-methyl-1,1-diphenyl-1-butanol from valine methyl ester, as in references cited in the Background of the Invention section of this application, and analogous methods may be used for other aminoalcohols starting with the appropriate aminoacid ester and Grignard reagent.

Many of the aminoacids are readily commercially available in optically active, i.e. non-racemic, form; and, for those aminoacids available in racemic form, resolution (by methods known to those of ordinary skill in the art such as the formation of diastereomeric salts with optionally active amines) may readily be performed to yield the aminoacid in the form of a single isomer for conversion to the aminoalcohol, or the racemic aminoalcohol (resulting from the reaction of a racemic aminoacid and a Grignard reagent) may itself be resolved by conventional methods. Suitable aminoacids include, e.g. leucine, valine, phenylalanine, α-phenylglycine, and the like, where $R^2$ is hydrogen, and preferred aminoacids include, e.g., proline, pipecolinic acid, 2-azetidinecarboxylic acid, 2-indolinecarboxylic acid, 1,2,3,4-tetrahydro-3-isoquinolinecarboxylic acid, and the like, where $R^2$ and $R^3$ form part of a ring. Esters of these aminoacids, if not commercially available, may readily be prepared by methods known to those of ordinary skill in the art.

Suitable Grignard reagents include phenylmagnesium chloride, tert-butylmagnesium chloride, cyclopentylmagnesium chloride, 2-mesitylmagnesium bromide (all of which are commercially available as solutions in diethyl ether, THF, or other suitable solvents), β-naphthylmagnesium bromide, and the like, which, if not commercially available, may readily be prepared by methods known to those of ordinary skill in the art.

Grignard reactions of this type are well-known, and are typically performed by slow addition of a solution of the Grignard reagent (usually in 5- to 10-fold excess) to a solution of the aminoacid ester at reduced temperature (e.g. at $-10°$ to $10°$ C., such as about $0°$ C.) under an inert atmosphere. The reaction mixture, after warming, is quenched with ice water, and the product aminoalcohol isolated, e.g. by extraction into an organic solvent, and purified, e.g. by crystallization.

It may be desirable in the preparation of Grignard reaction, as described above, of the β- and γ-aminoalcohol precursors to the catalysts of this invention to protect the nitrogen of the aminoacid by the use of such protecting groups as are conventional in the art for the protection of aminoacid nitrogen atoms, for example benzyloxycarbonyl, t-butoxycarbonyl, fluoren-9-ylmethoxycarbonyl, and the like. Such protection of the nitrogren atom may be done by methods known to those of ordinary skill in the art.

Suitable chiral γ-aminoalcohols are of the formula:

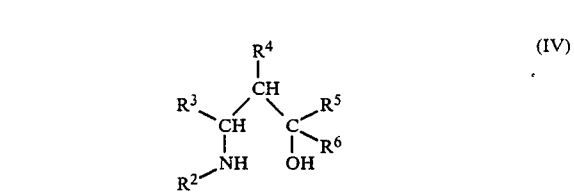

(IV)

in which:
$R^2$ is hydrogen, methyl, or ethyl;
$R^3$ is alkyl, aryl, or aralkyl; or $R^2$ and $R^3$, taken together with that part of the aminoalcohol to which they are attached, form a 4-, 5-, or 6-membered ring;
$R^4$ is hydrogen, alkyl, or aryl; or $R^2$ and $R^4$, taken together with that part of the aminoalcohol to which they are attached, form a 5- or 6-membered ring; and
$R^5$ and $R^6$ are independently alkyl, aryl, or aralkyl; or $R^2$ and $R^5$, taken together with that part of the aminoalcohol to which they are attached, form a 6-membered ring and $R^6$ is hydrogen.

Preferred aminoalcohols of formula IV are those in which one or (preferably) more than one of the following are true:

(1) $R^2$ forms part of a ring with $R^3$, $R^4$, or $R^5$, or is hydrogen;

(2) $R^3$ forms part of a ring with $R^2$, or is bulky alkyl, aryl, or aralkyl;

(3) $R^4$, is not forming part of a ring with $R^2$, is hydrogen or lower alkyl, preferably hydrogen; or (4) $R^5$, is not forming part of a ring with $R^2$ (in which case $R^6$ is hydrogen), and $R^6$ are bulky alkyl, aryl, or aralkyl, and are more preferably the same (for ease of synthesis).

Particularly preferred aminoalcohols of formula IV are those in which:

(1) $R^2$ and $R^3$, taken together with that part of the aminoalcohol to which they are attached, form a 4-, 5-, or 6-membered ring, more preferably a 4- or 5-membered ring; and (2) $R^4$ is hydrogen or lower alkyl, preferably hydrogen; and (3) $R^5$ and $R^6$ are bulky alkyl, aryl, or aralkyl, and are more preferably the same (for ease of synthesis).

In the case where $R^5$ does not form part of a ring, $R^5$ and $R^6$ are preferably the same and the aminoalcohols may be most conveniently prepared by the reaction of an ester, typically a lower alkyl ester, of a β-aminoacid with a Grignard reagent of the form $R^5$ MgX (where X is halogen) in the manner described previously for the synthesis of the analogous β-aminoalcohols.

Certain of the β-aminoacids suitable for the synthesis of the chiral γ-aminoalcohol precursors to the catalysts of the invention are commercially available, such as 3-aminobutyric acid, 3-amino-3-phenylpropionic acid, and nipecotic acid (3-piperidinecarboxylic acid), while others may be prepared by methods known to those of ordinary skill in the art. For example, 2-pyrrolidineactic acid may be prepared by the method of T. Wakabayashi et al., Synth. Comm., 7, 239 (1977), and 2-piperidineacetic acid by the method of W. D. Marshall et al., Can. J. Chem., 53, 51 (1975).

Other chiral γ-aminoalcohols include cis-2-phenyl-4-hydroxypiperidine (which may be prepared by the Michael addition of O-benzylhydroxylamine to methyl vinyl ketone to yield 2-(benzyloxyamino)ethyl methyl ketone, followed by an intramolecular Mannich reaction with benzaldehyde to yield 1-benzyloxy-4-oxo-2-phenylpiperidine, reduction with sodium borohydride to the corresponding 4-hydroxy compound, removal of the N-benzyloxy group with hydrogen and palladium catalyst, and resolution of the resulting 4-hydroxy-2-phenylpiperidine with the use of an optionally active acid, such as mandelic acid) and the like.

EXAMPLES

The following examples illustrate the catalyst and reduction process of the invention, but should not be construed to limit it.

EXAMPLE 1

Preparation of
(S)-(−)-α,α-diphenyl-2-pyrrolidinemethanol

A. N-Benzyloxycarbonyl-(S)-proline

A 500-mL, three-necked, round-bottomed flask was equipped with two pressure equalizing dropping funnels (50- and 100-mL), a thermometer, and a magnetic stirrer. The flask was charged with 100 mL (0.2 mol) of a 2M aqueous solution of sodium hydroxide, and cooled with an ice-salt bath. To the aqueous solution 23.0 g (0.2 mol) of (S)-proline (Aldrich) was added at 0°∼−5° C. with stirring. To the resulting solution 36.4 ml (40.9 g, 0.24 mol) of benzyl chloroformate (Aldrich) and 70 mL (0.28 mole) of a 4M aqueous solution of sodium hydroxide was added dropwise during 1 hr at 0°∼−5° C., under vigorous stirring. The reaction mixture was stirred for another 1 hr at 0°∼−5° C., and then washed with ethyl ether (2×50 mL). The aqueous solution was carefully acidified to pH 2 by a dropwise addition of 6M hydrochloric acid with cooling under stirring. The resulting mixture was saturated with sodium sulfate and extracted with ethyl acetate (3×100 mL). The extracts were combined, dried over anhydrous sodium sulfate (2 changes), and evaporated under reduced pressure to give 58.7 g of colorless oil. This oil was dissolved in 50 mL of ethyl acetate, and to this solution 200 mL of petroleum ether (bp 35°–60° C.) was added to separate an oil. The mixture was cooled with an ice-bath, and the wall of the flask was continuously scratched with a glass rod until the whole oil was crystallized. The crystals were collected on a glass filter and washed with 20 mL of petroleum ether. After drying under vacuum, 47.9 g (0.192 mol) Of N-benzyloxycarbonyl-(S)-proline was obtained as white crystals, mp 69°–74° C., $[\alpha]_D^{22}$ −39.9° C. (ethanol, c 2.0), 96% yield.

B. N-Benzyloxycarbonyl-(S)-proline methyl ester

A dry 1-L, one-necked, round-bottomed flask was equipped with a Liebig condenser fitted with a rubber septum and a magnetic stirrer. The condenser was temporarily removed, and the flask was charged with 33.7 g (0.135 mol) of N-benzyloxycarbonyl-(S)-proline and 400 mL of anhydrous methanol (Mallinckrodt). The flask was flushed with nitrogen through the septum. The mixture was stirred, and 24.6 mL (28.4 g, 0.2 mol) of boron trifluoride etherate was added via cannula. The resulting mixture was stirred and refluxed for 1 hr under nitrogen. After the solvent was removed under reduced pressure, the residue was vigorously stirred with 200 mL of ice-water. The mixture was extracted with ethyl acetate (3×100 mL). The extacts were combined and successively washed with brine (2×20 mL), a 1M aqueous sodium hydrogen carbonate solution (3×20 mL), and brine (2×20 mL), and dried over anhydrous sodium sulfate. After the removal of the solvent under reduced pressure, a colorless oil was obtained. The oil was dissolved in 100 mL of dry toluene (distilled over CaH₂), and the solvent was removed under reduced pressure to remove water from the oil. This treatment was repeated to give 35.9 g of N-benzyloxycarbonyl-(S)-proline methyl ester is a colorless oil (containing a small amount of toluene), $[\alpha]_D^{21}$ −53.9° (methanol, c 1.0).

C. (S)-(−)-α,α-diphenyl-2-pyrrolidinemethanol

A dry 1-L three-necked, round-bottomed flask was equipped with a pressure equalizing 250-mL dropping funnel, a thermometer, a rubber septum, and a large magnetic stirrer. The flask was flushed with nitrogen and charged with 400 mL (0.8 mol) of phenylmagnesium chloride tetrahydrofuran solution (2M) (Aldrich). A separate dry 250-mL flask was charged with 26.3 g (0.1 mol) of N-benzyloxycarbonyl-(S)-proline methyl ester and flushed with nitrogen. To the ester 100 mL of dry tetrahydrofuran (distilled over sodium-benzophenone) was added and stirred under nitrogen. The tetrahydrofuran solution of the ester was transferred to the dropping funnel using a double-ended needle and added to the phenylmagnesium chloride tetrahydrofuran solution during 0.5∼1 hr at 0°∼−10° C. with ice-salt bath cooling under nitrogen. After the addition the cooling bath was removed and the reaction mixture was allowed to warm to room temperature, and stirred overnight under nitrogen. The reaction mixture was hydrolyzed by pouring it with frequent shaking into a 2-L round bottomed flask containing 300 g of crushed ice and a solution of 60 g of ammonium chloride in 100 mL of water. The resulting mixture was evaporated under reduced pressure to remove the tetrahydrofuran, and the resulting aqueous mixture was extracted with ethyl ether (4×200 mL). The organic layers were combined, washed with brine (2×30 mL), dried over anhydrous potassium carbonate, and concentrated in a rotary evaporator to a total volume of 500 mL. Dry hydrogen chloride gas was bubbled into the solution with stirring until the mixture was acidic. The hydrochloride precipitate was filtered, washed with ethyl ether (2×50 mL). The hydrochloride was suspended in 300 mL of ethyl ether, and to this suspension 60 mL of a 2M sodium hydroxide aqueous solution was added with vigorous stirring. The resulting mixture was stirred vigorously for 45 min to liberate the desired aminoalcohol. The mixture was separated and the aqueous solution was extracted with ethyl ether (2×50 mL). The organic extracts were combined, washed with brine (3×30 mL), dried over anhydrous potassium carbonate, and evaporated under reduced pressure to give crude crystals. The crystals were recrystallized from methanol (15 mL) and water (3 mL), and the resulting crystals were collected and dried in a desiccator under reduced pressure to give 13.3 g (0.0527 mol, 52.7% yield) of (S)-(−)-α,α-diphenyl-2-pyrrolidinemethanol as colorless crystals, mp 76.5°~77.5° C., $[\alpha]_D^{24}$ −58.8° (methanol, c 3.0), enantiomeric excess 99.4% (measured by HPLC of the (S)-(+)-MTPA amide), $^1$H NMR (CDCl$_3$) δ: 1.8–1.5 (m, 4H, CH$_2$) 2.9–3.1 (m, 2H, CH$_2$N) 4.25 (m, 1H, NCH) 2–5 (broad peak, 2H, OH, NH) 7.1∝7.6 (m, 10H, ArH);

IR (Nujol) ν: 3360, 3060, 1595, 1490, 1450, 1395, 1190, 1105, 1065, 1065, 1035, 990, 755, 710, 700, 660, 640 cm$^{-1}$.

D. Proceeding in a similar manner, but substituting for (S)-proline other α-aminoacids such as
(S)-(−)-2-azetidinecarboxylic acid,
(S)-(−)-pipecolinic acid,
(S)-(−)-1,2,3,4-tetrahydro-3-isoquinolinecarboxylic acid,
(S)-(+)-leucine,
(S)-(+)-valine,
(S)-(−)-phenylalanine, and the like,
or β-aminoacids such as
(S)-2-pyrrolidineacetic acid,
(S)-2-piperidineacetic acid, and the like;
and substituting for phenylmagnesium chloride other Grignard reagents such as
4-tolylmagnesium chloride,
t-butylmagnesium bromide,
2-naphthylmagnesium bromide, and the like;
there are prepared other β- or γ-aminoalcohols such as
(S)-(−)-α,α-diphenyl-2-azetidinemethanol,
(S)-(−)-α,α-di(2-naphthyl)-2-pyrrolidinemethanol,
(S)-(−)-α,α-di(4-tolyl)-2-piperidinemethanol,
(S)-(−)-α,α-diphenyl-1,2,3,4-tetrahydro-3-isoquinolinemethanol,
(S)-(+)-2-amino-4-methyl-1,1-di(t-butyl)-1-pentanol,
(S)-(+)-2-amino-3-methyl-1,1-di(4-tolyl)-1-butanol,
(S)-(−)-2-amino-1,1,3-triphenyl-1-propanol,
(S)-β,β-diphenyl-2-pyrrolidineethanol,
(S)-β,β-di(t-butyl)-2-piperidineethanol, and the like.

EXAMPLE 2

Preparation of (S)-5,5-diphenyl-3,4-propano-1,3,2-oxazaborolidine

A. (S)-(−)-α,α-diphenyl-2-pyrrolidinemethanol (378.5 mg, 1.5 mmol) was dissolved in 4.09 mL (4.5 mmol) of BH$_3$.THF (1.1M), and the resulting solution was refluxed for 48 h under argon atmosphere (1 bar). The solvent was removed under vacuum, and the residue was sublimed (150°–160° C./0.1 Torr) to give 258 mg of a crude product. This product (94.1 mg) was resublimed (145°–160° C./0.05 Torr) to give 36.7 mg (0.139 mmol), 25.4% yield) of (S)-5,5-diphenyl-3,4-propano-1,3,2-oxazaborolidine as colorless crystals, mp 107°–124° C., MS (EI) m/z 263 (M+, 20%), 234 (5%), 193 (7%), 165 (13%), 84 (100%).

M+263.14826 (calcd. 263.14814), $^1$H NMR (0.39M in C$_6$D$_6$) δ: 6.9–7.70 (m, 10H, phenyl) 4.42 (dd, J=6.0, J=4.6, 1H, N—CH(C)—C) 3.02–3.16 (m, 2H, N—CH$_2$—C) 1.61–1.70 (m, 2H, N—C(C)—CH$_2$—C), $^{11}$B NMR (0.17M in THF) +28.3 ppm (broad s, narrowed by $^1$H decoupling) +7.6 ppm (d, J$_{BH}$ 130 Hz) (dimer), IR (0.1M in THF) 2568 cm$^{-1}$ (BH) (monomer), 2413 cm$^{-1}$ (BH) (dimer).

B. Proceeding in a similar manner, but substituting for (S)-(−)-α,α-diphenyl-2-pyrrolidinemethanol other β- or γ-aminoalcohols such as
(S)-(−)-α,α-diphenyl-2-azetidinemethanol,
(S)-(−)-α,α-di(2-naphthyl)-2-pyrrolidinemethanol,
(S)-(−)-α,α-di(4-tolyl)-2-piperidinemethanol,
(S)-β,β-diphenyl-2-pyrrolidineethanol,
(S)-β,β-di(t-butyl)-2-piperidineethanol, and the like,
there are obtained
(S)-5,5-diphenyl-3,4-ethano-1,3,2-oxazaborolidine,
(S)-5,5-di(2-naphthyl)-3,4-propano-1,3,2-oxazaborolidine,
(S)-3,4-butano-5,5-di(4-tolyl)-1,3,2-oxazaborolidine,
(S)-2H,4H,5H,6H-6,6-diphenyl-3,4-propano-1,3,2-oxazaborine,
(S)-2H,4H,5H,6H-3,4-butano-6,6-di(t-butyl)-1,3,2-oxazaborine, and the like.

EXAMPLE 3

Preparation of (S)-5,5-diphenyl-2-methyl-3,4-propano-1,3,2-oxazaborolidine

A. A solution of (S)-(−)-α,α-diphenyl-2-pyrrolidinemethanol (3.4 g, 13.5 mmol) and methylboronic acid (0.89 g, 14.83 mmol) in toluene (40 mL) was refluxed under argon for 3 hr using a Dean-Stark apparatus to remove water. The solvent was removed under reduced pressure and the residue was evaporatively distilled using a Kugelrohr apparatus (170° C./0.1 mm) to afford (S)-5,5-diphenyl-2-methyl-3,4-propanol-1,3,2-oxazaborolidine (3.2 g, 11.54 mmol, 85.5% yield), mp 74°–87° C.

$^{11}$B NMR (0.075M on THF, BF$_3$.Et$_2$O as internal standard) +33.51 ppm (due to monomer) +7.94 ppm (due to dimer).

B. Proceeding in a similar manner, but substituting for (S)-(−)-α,α-diphenyl-2-pyrrolidinemethanol other β- or γ-aminoalcohols such as
(S)-(−)-α,α-diphenyl-2-azetidinemethanol,
(S)-(−)-α,α-di(4-tolyl)-2-piperidinemethanol, (S)-β,β-diphenyl-2-pyrrolidineethanol,
(S)-β,β-di(t-butyl)-2-piperidineethanol, and the like, there are obtained (S)-5,5-diphenyl-3,4-ethano1-2-methyl-1,3,2-oxazaborolidine, (S)-3,4-butano-5,5-di(4-tolyl)-2-methyl-1,3,2-oxazaborolidine, (S)-2H,4H,5H,6H-6,6-diphenyl-2-methyl-3,4-propano-1,3,2-oxazaborine, (S)-2H,4H,5H,6H-3,4-butano-6,6-di(t-butyl)-2-methyl-1,3,2-oxazaborine, and the like; and other B-(lower alkyl) compounds are prepared with the use of the appropriate (lower alkyl)boronic acid, to afford compounds such as (S)-2-n-butyl-5,5-diphenyl-3,4-propano-1,3,2-oxazaborolidine, (S)-5,5-diphenyl-2-(3-phenylpropyl)-3,4-propano-1,3,2-oxazaborolidine, (3S,2′R)-5,5-diphenyl-2-(2′-(6-methoxy-2-naphthyl)-propyl)-3,4-propano-1,3,2-oxazaborolidine, and the like.

EXAMPLE 4

Preparation of tricyclic oxazaborolidines derived from cis-2-azabicyclo[3.3.0]octan-2-one The preparation of (±)-(1R*,5S*,8R*)-2-aza-8-phenylbicyclo[3.3.0]octan-8-ol (compound 1a) and the corresponding 8-(2-naphthyl) analog (Compound 1b) are as shown in Scheme 1.

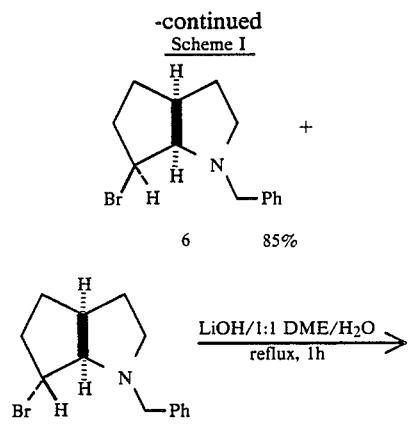

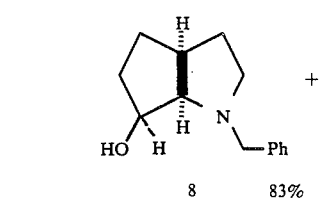

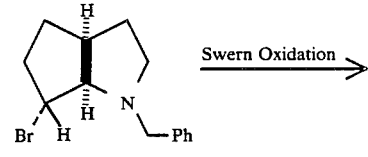

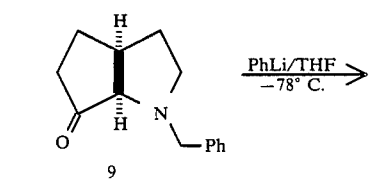

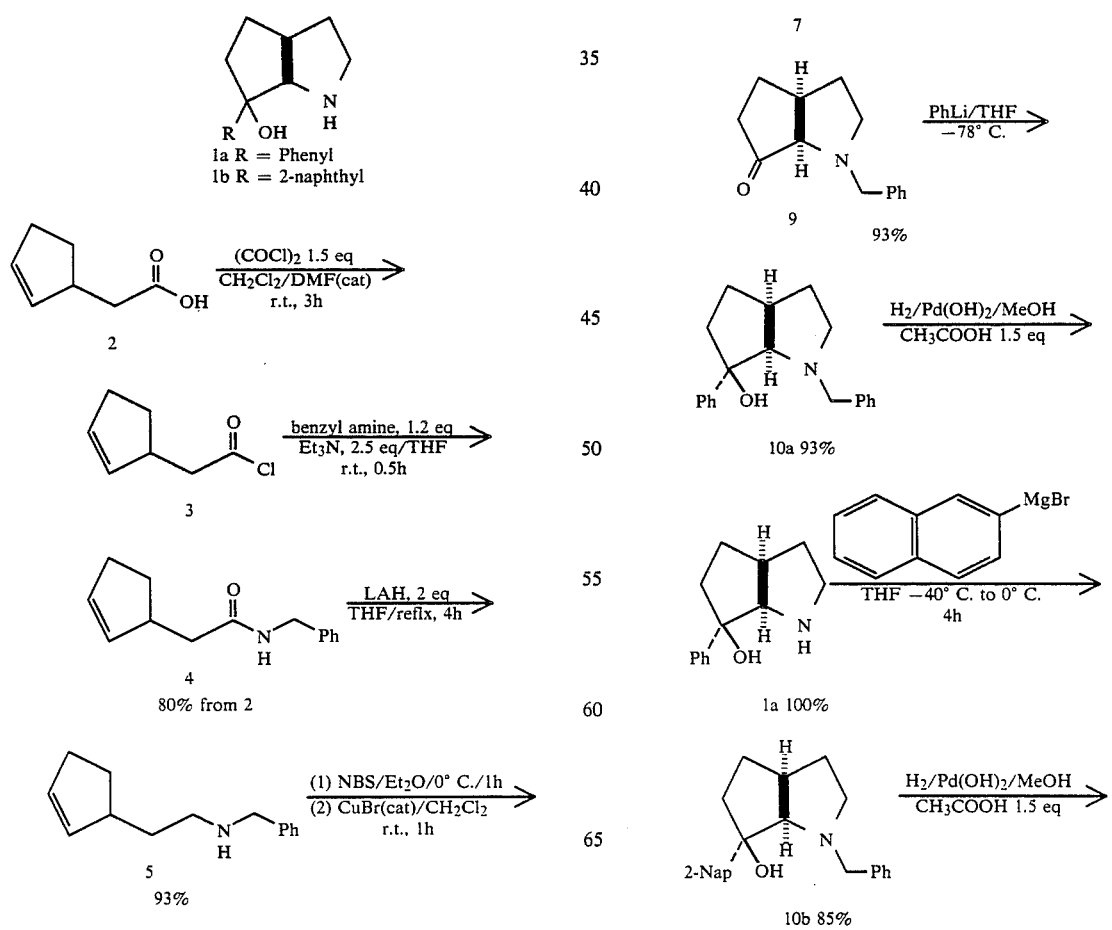

-continued
Scheme I

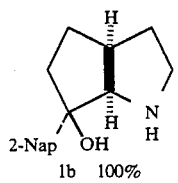

1b 100%

A. N-Benzyl-cis-2-azabicyclo[3.3.0]octan-8-one (9)

The commerically available 2-cyclopentene-1-acetic acid was treated with oxalyl chloride in $CH_2Cl_2$. The reaction was catalyzed with a drop of DMF; and stirring for 2 h afforded a quantitative yield of 3 as a light brown oil. Crude 3 was treated with benzylamine in THF (using $Et_3N$ as a base) to afford 4 as a yellow solid, which was purified by recrystallization (hexane/$CH_2Cl_2$). Reduction of 4 with lithium aluminum hydride under reflux conditions gave 5 as a light brown oil. Crude 5 was brominated with N-bromosuccinimide; and cuprous bromide cyclization afforded 6 and 7 in 10:1 ratio. The crude mixture of 6 and 7 was hydrolyzed in LiOH/DME/water under reflux to afford 8 as a light yellow oil. Swern oxidation of 8 gave 9, a light brown oil, as the key intermediate, IR (neat) 2950, 2800, 1740, 700 cm$^{-1}$, $^1$H NMR (CDCl$_3$) δ: 7.35–7.2 (n, 5H) 4.19 (d, 1H, J=13 Hz) 3.50 (m, 1H, J=13 Hz) 2.92 (d of t, 1H, J=7, 1.89 Hz) 2.9–2.75 (m, 2H) 2.65–2.55 (m, 1H) 2.35 (q, 1H, J=6.6 Hz) 2.25–2.15 (m, 1H) 2.15–2.0 (m, 2H) 1.85–1.75 (m, 1H) 1.65–1.55 (m, 1H), TLC (1:5 ether/hexane)
R$_f$=0.45.

B. (±)-(1R*,5S*,8R*)-2-aza-8-phenylbicyclo[3.3.0]octan-8-ol (1a)

In a round bottomed flask equipped with a magnetic stirrer and N$_2$ inlet was dissolved 9 (2.15 g, 10 mmol) in THF (50 mL) and cooled to −78° C. A solution of phenyllithium (1.34M, 9 mL, 1.2 eq) was added to the solution over 2 min, and the solution stirred at −78° C. for 1 h. TLC showed no starting material was left. The resulting mixture was worked up with water (10 mL); concentrated in vacuo; and extracted with CH$_2$Cl$_2$ (3×50 mL). The combined organic layer was washed with brine (50 mL); dried (Na$_2$SO$_4$); and concentrated in vacuo to afford a light brown oil. Flash column chromatography (20% ether/80% hexane) afforded 2.37 g 10a (93%) as a light yellow oil.

In a round bottomed flask equipped with magnetic stirrer and H$_2$ inlet were mixed 10a (1.47 g, 5 mmol), acetic acid (1.42 mL, 1.5 eq) and 10% Pd(OH)$_2$ (150 mg) on carbon in MeOH (20 mL). The solution was degassed three times under H$_2$ (1 atm) and stirred for 2 h. TLC showed no starting material was left. The resulting mixture was filtered through celite; concentrated in vacuo; extracted with CH$_2$Cl$_2$ (3×30 mL) and 2N NaOH (30 mL). The combined organic layer was washed with brine (50 mL); dried (Na$_2$SO$_4$); and concentrated in vacuo to afford 1.02 g 1a (100%) as a white solid. The solid was recrystallized with EtOH/H$_2$O to afford 1a as colorless crystals, m.p. 66°–66.5° C., IR (neat) 3600–3200 (br) 2952, 2867, 1445, 700 cm$^{-1}$.

$^1$H NMR (CDCl$_3$) δ: 7.47–7.46 (m, 2H) 7.33–7.30 (m, 2H) 7.20 (t, 1H, J=7.3 Hz) 5.7–5.0 (br, 1H) 3.78 (d, 1H, J=9.5 Hz) 3.12–3.02 (m, 2H) 2.88–2.80 (m, 1H) 2.18–2.0 (m, 2H) 2.0–1.85 (m, 2H) 2.0–1.3 (br, 1H) 1.7–1.6 (m, 2H),

TLC (ether)
R$_f$=0.2.

C. (±)-(1R*,5S*,8R*)-2-aza-8-(2-naphthyl)bicyclo[3.3.0]octan-8-ol (1b)

The title compound was prepared in a similar manner to the phenyl analog in part B above using 2-naphthylmagnesium bromide instead of phenyllithium for reaction with the ketone. Other alkyl, aralkyl, or aryl analogs of compounds 1a and 1b are prepared in a similar fashion from the ketone using Grignard reagents, aryllithium, etc. as appropriate.

D. Resolution of the bicyclic aminoalcohols

The bicyclic aminoalcohols 1a and 1b were resolved as shown in Scheme II using conventional techniques to afford their individual optical isomers, with DAG (2,3:4,6-di-O-isopropylidene-2-keto-L-gulonic acid) as resolving agent for the phenyl compound (1a) and dibenzoyltartaric acid for the naphthyl compound (1b). Alternative resolving agents may be used, if desired; and the choice of a resolving agent for another of the bicyclic aminoalcohols will pose no difficulty for one of ordinary skill in the art, having regard to his own knowledge and this disclosure.

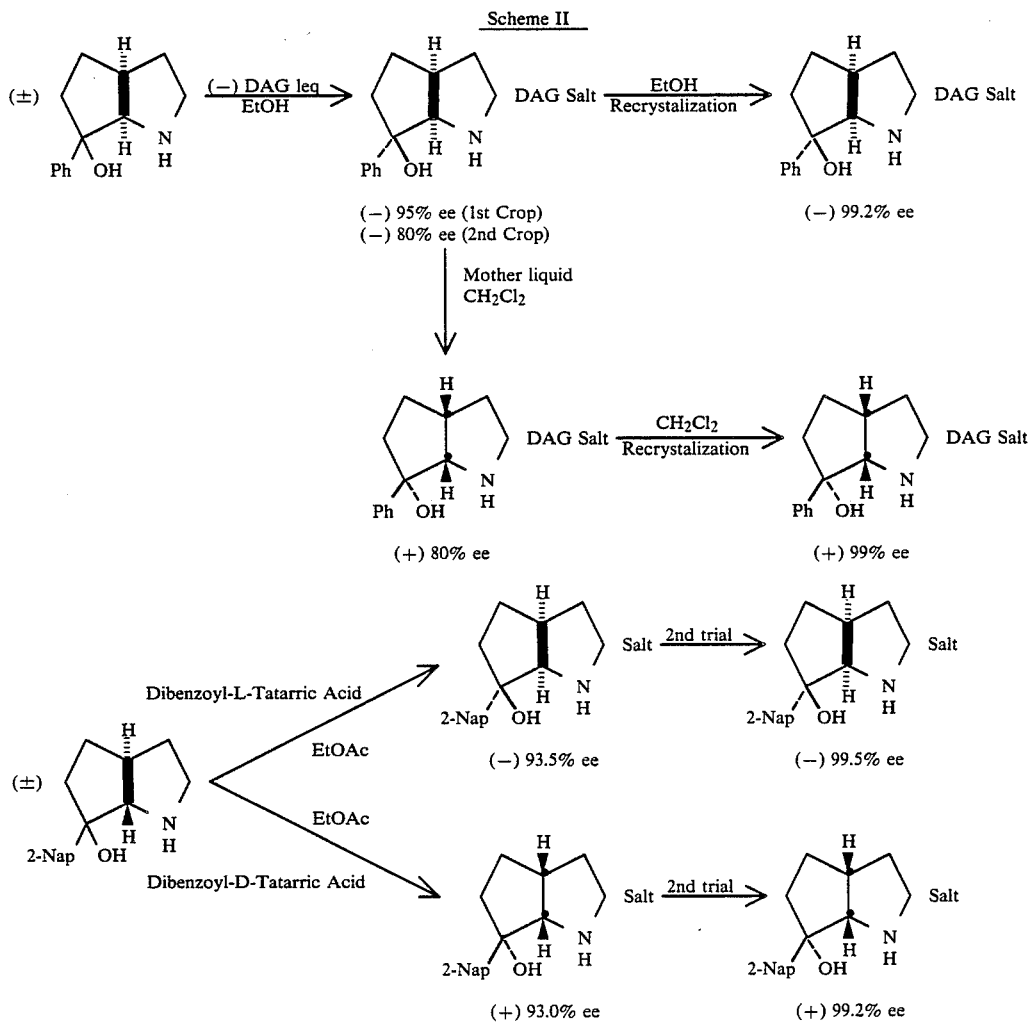

E. Preparation of the tricyclic oxazaborolidine catalysts

The tricyclic oxazaborolidine catalysts were prepared from the resolved aminoalcohols using the techniques set forth in Examples 2 and 3, to afford the tricyclic N-methyl-, N-n-butyl-, and N-(R)-2-(6-methoxy-2-naphthyl)propyloxazaborolidines. Other N-substituted or unsubstituted oxazaborolidines are prepared in similar fashion.

EXAMPLE 5

Catalytic reduction of prochiral ketones

A. Reduction of acetophenone with (S)-5,5-diphenyl-4-isopropyl-1,3,2-oxazaborolidine (1) and BH$_3$.THF 1 (3.3 mg, 0.0125 mmol) was dissolved in 2.73 mL (3 mmol) of BH$_3$.THF (1.1M) and stirred at room temperature. To this solution 300.4 mg (2.5 mmol) of acetophenone in 2.5 mL of dry THF was added dropwise (8 min). The reaction was followed by TLC (n-hexane:ethyl acetate 8:2). It showed the complete conversion of the prochiral ketone (R$_f$0.47) to the corresponding alcohol (R$_f$0.27) within 2 min of the addition. After 10 min the reaction mixture was decomposed by the addition of 2M HCl (1.5 mL, 10 min). The reaction mixture was diluted with 20 mL of ether, washed with brine (1 mL×3), saturated aqueous NaHCO$_3$ (2 mL×3), and brine (1 mL×3) successively. The ether solution was dried over MgSO$_4$ and evaporated to give 316.2 mg of colorless oily residue.

The ratio of alcohol to unchanged prochiral ketone in the residue was determined by GLC analysis (200° C.) as described above to be alcohol:unchanged prochiral ketone 99.8:0.1.

The oily residue (187.3 mg) was distilled (bulb to bulb, bath temperature: 120°–130° C./20 Torr) to give 166 mg of colorless oil (91.7% yield from the ketone). This oil was identified to be 1-phenylethanol by $^1$H NMR and IR spectroscopy. The optical rotation was $[\alpha]_D^{22}+30.5°$ (c 2.23, CH$_2$Cl$_2$), lit. $[\alpha]_D^{22}-52.5°$ (c 2.27, CH$_2$Cl$_2$) (S). The enantiomeric excess of the alcohol was determined by GLC of the menthyloxycarbonyl derivative to be 59.0%.

B. Reduction of acetophenone with (S)-5,5-diphenyl-3,4-propano-1,3,2-oxazaborolidine (2) and BH$_3$.THF and recovery of the chiral aminoalcohol 2 (39.5 mg, 0.15 mmol) was dissolved in 3.27 mL (3.6 mmol) of BH$_3$.THF (1.1M) and stirred at room temperature (23° C.). To this solution 721 mg (6 mmol) of acetophenone in 6 mL of dry THF was added dropwise (6 min). The reaction was followed by TLC (n-hexane:ethyl acetate 8:2). It showed the complete conversion of the prochiral ketone ($R_f$ 0.49) to the corresponding alcohol ($R_f$ 0.27) within 2 min of the addition. After 20 min the reaction mixture was decomposed by the addition of methanol until no hydrogen evolution was observed (350 μl, 50 min). The mixture was evaporated to give a colorless oily residue. This residue was transferred to a centrifuge tube (5 mL) with 1.5 mL of ether. To this ether solution, saturated HCl-ether solution (anhydrous) was added with stirring until no more precipitate (white) formation was observed (40 μl, <pH 3-5). The suspension was separated by centrifugation into a white precipitate and a supernatant (colorless), and the supernatant containing the reduced alcohol was removed. The precipitate was washed with ether followed by centrifugation (3 mL×3), and the ether solutions were combined. This ether solution was diluted with 20 mL of ether and washed with brine (1 mL×3). The ether solution was dried over $MgSO_4$, and evaporated to give 701.1 mg of colorless oily residue.

The ratio of alcohol to unchanged prochiral ketone in the residue was determined by GLC to be alcohol:prochiral ketone 99.86:0.14.

The residue (151.8 mg) was distilled (bulb to bulb, bath temperature: 120°-135° C./20 Torr) to give 141.8 mg (89.4% yield from the ketone) of colorless oil. This oil was identified to be 1-phenylethanol by $^1$H NMR and IR spectroscopy: $[\alpha]_D^{24} +49.8°$ (c 2.25, $CH_2Cl_2$), lit. $[\alpha]_D^{22} -52.5°$ (c 2.27, $CH_2Cl_2$) (S). This oil (12.2 mg, 0.1 mmol) was converted to the menthyloxycarbonyl derivative, and the diastereomeric excess of the derivative was determined by GLC to be 94.9% [170° L C., retention times: 6.90 (minor) and 7.33 min (major)].

Recovery of the chiral amino alcohol was carried out as follows: to the white precipitate, which was obtained as described above, 2M NaOH (0.2 mL) was added and stirred vigorously. The aqueous mixture was extracted with ether (3 mL×3). The ether solutions were combined, washed with brine (0.5 ml×3), dried over $MgSO_4$, and evaporated to give 40.3 mg of crystals. These crystals were identified as α,α-diphenyl-2-pyrrolidinemethanol by $^1$H NMR and IR spectroscopy. The enantiomeric excess of this amino alcohol was determined as described above to be 99.5% [absolute configuration (S)].

C. Reduction of propiophenone with 2 and $BH_3.THF$

Method I (Addition of propionphenone to the mixture of 2 and $BH_3$.THF): To a solution of 2 (14 mg, 0.0532 mmol) in $BH_3$.THF (1.1M, 0.58 mL, 0.638 mmol, 12 eq.) was added slowly dropwise a THF solution (1 mL) of propiophenone (142.7 mg, 1.064 mmol, 20 eq.) in 7 min at room temperature (23° C.). After stirring the reaction mixture for 2 min, the excess of hydride was decomposed by addition of 2M HCl (0.5 mL). The reaction mixture was diluted with ethyl ether (50 mL), washed with brine (25 mL×2), saturated $NaHCO_3$ (25 mL×2), and brine (25 mL×2). The organic extract was dried over anhydrous $MgSO_4$ and solvent removed under vacuum to afford crude alcohol (104 mg, 99.58%, GLC conversion). The alcohol was distilled (bulb to bulb, bath temperature: 120°-130° C./20 Torr) and rotation recorded ($[\alpha]_D^{23} +38.7°$ (c 5, $C_6H_6$), lit. $[\alpha]_D +40.05°$ (c 5, $C_6H_6$).

GLC of the menthyloxycarbonyl derivative indicated the optical purity to be 88.5% e.e. (89.5% corrected) [170° C., retention times for diastereomers were 8.74 (minor) and 9.37 min (major)].

Method II. (Addition of $BH_3$.THF to the mixture of 2 and propiophenone (Inverse addition)): To a solution of 2 (13 mg, 0.494 mmol) in THF (1 mL) at −10° C. (ice/acetone bath) was added propionphenone (132 mg, 0.988 mmol, 20 eq.). After stirring for few minutes, $BH_3$.THF (1.1M, 0.538 mmol, 12 eq.) was added dropwise in 7 min. The reaction mixture was further stirred for 7 min and excess hydride was decomposed by addition of 2M HCl (0.5 mL). The reaction mixture was diluted with ether (100 mL), washed with brine (25 mL), saturated $NaHCO_3$ (25 mL×2), and brine (25 mL×2). The organic extract was dried over anhydrous $MgSO_4$ and solvent removed to afford crude alcohol (144 mg).

GLC of the menthyloxycarbonyl derivative indicated the optical purity to be 89.03% e.e. (90.0% corrected).

D. Reduction of chloroacetophenone with 2 and $BH_3.THF$

To a solution of 2 (13 mg, 0.049 mmol) in $BH_3$.THF (1.1M, 0.538 mL, 0.598 mmol, 12 eq.) was added dropwise a solution of chloroacetophenone (152 mg, 0.988 mmol, 20 eq.) (recrystallized from $CCl_4$) in THF (1 mL) over the period of 5 to 6 min. After stirring the reaction mixture for 2 min, excess hydride was decomposed by addition of 2M HCl (0.5 mL). The reaction mixture was diluted with ether (100 mL) and washed with brine (25 mL×2). The organic extract was dried over anhydrous $MgSO_4$ and the solvent removed to afford crude alcohol (160 mg), which was distilled (bulb to bulb, bath temperature: 105° C./0.5 Torr) to afford pure alcohol: $[\alpha]_D^{23} +49.32°$ (c 2.8, cyclohexane), lit. $[\alpha]_D -47.8°$ (c 2.8, cyclohexane) (R)-enantiomer.

GLC of the menthyloxycarbonyl derivative indicated the optical purity to be 96.3% e.e. [97/3% corrected], [175° C., retention times 11.83 (minor) and 12.42 min (major)].

E. The results of a number of reductions using the process of the invention with (S)-5,5-diphenyl-3,4-propano-1,3,2-oxazaborolidine (2) as catalyst are shown in Table I.

TABLE I

Borane Reduction of Prochiral Ketones Catalyzed by 2

$$2\ R_S R_L CO + BH_3 \xrightarrow{2,\ THF} (R_S R_L CH-O)_2 BH \longrightarrow R_S R_L CHOH$$

| Prochiral Ketone | Equiv $BH_3$ | Equiv 2 | Reaction time (min) | temp (°C.) | Config. of Product[a] (% ee)[b,c] |
|---|---|---|---|---|---|
| $C_6H_5COCH_3$ | 2 | 1 | 2 | 30 | R(95.8) |
| $C_6H_5COCH_3$ | 1 | 0.1 | 2 | 30 | R(96.1)* |
| $C_6H_5COCH_3$ | 1.2 | 0.025 | 2 | 23 | R(93.5) |
| $C_6H_5COCH_3$ | 0.6 | 0.025 | 2 | 23 | R(94.9) |
| $C_6H_5COCH_3$ | 1.2 | 0.05 | 2 | 23 | R(78.8) |
| $C_6H_5COCH_3$ | 1.2 | 0.025 | 2 | 0 | R(81.5) |
| $C_6H_5COCH_3$ | 1.2 | 0.025 | 30 | −20 | R(83.0) |
| $C_6H_5COC_2H_5$ | 1.2 | 0.05 | 2 | 23 | R(85.0) |
| $C_6H_5COC_2H_5$ | 1 | 0.05 | 2 | 23 | R(87.1) |
| $C_6H_5COC_2H_5$ | 0.6 | 0.05 | 2 | 23 | R(88.5) |
| $C_6H_5COC_2H_5$ | 0.6 | 0.1 | 5 | −10 | R(89.3)[d*] |
| $C_6H_5COC_2H_5$ | 0.6 | 0.05 | 5 | −10 | R(89.0)[d] |
| t-BuCOCH_3 | 1.2 | 0.05 | 2 | 23 | R(73.8) |
| t-BuCOCH_3 | 1.2 | 0.05 | 2 | 0 | R(60.5) |
| t-BuCOCH_3 | 1 | 0.05 | 2 | 23 | R(79.7) |
| t-BuCOCH_3 | 0.6 | 0.05 | 2 | 23 | R(86.8) |
| t-BuCOCH_3 | 0.6 | 0.1 | 2 | −10 | R(90.8)[d*] |
| α-tetralone | 0.6 | 0.05 | 2 | 23 | R(88.4)* |
| α-tetralone | 0.6 | 0.1 | 2 | −10 | R(88.4)[d] |

TABLE I-continued
Borane Reduction of Prochiral Ketones Catalyzed by 2

$$2\ R_S R_L CO + BH_3 \xrightarrow{2,\ THF} (R_S R_L CH-O)_2 BH \longrightarrow R_S R_L CHOH$$

| Prochiral Ketone | Equiv BH$_3$ | Equiv 2 | Reaction time (min) | temp (°C.) | Config. of Product$^a$ (% ee)$^{b,c}$ |
|---|---|---|---|---|---|
| C$_6$H$_5$COCH$_2$Cl | 0.6 | 0.05 | 2 | 23 | S(96.3)* |

Notes:
$^a$For each entry, conversion of the prochiral ketone to the alcohol was >99.7%.
$^b$The absolute configuration was determined by isolation and measurement of rotation; the e.e. was determined by GLC.
$^c$The optical purity of the aminoalcohol was 99%, and therefore the optical purity of the alcohol should be corrected by 1%.
$^d$BH$_3$.THF was added to a mixture of catalyst and prochiral ketone in THF at −10° C.
*Opitmal conditions.

F. Reduction of 6-methoxy-2-acetylnaphthalene with (S)-5,5-diphenyl-2-methyl-3,4-propano-1,3,2-oxazaborolidine (3) and BH$_3$.THF To a solution of 3 (692 mg, 2.496 mmol) in BH$_3$.THF (1.1M, 13.63 mL, 15 mmol) was added slowly a solution of 6-methoxy-2-acetylnaphthalene (5 g, 25 mmol) in THF (25 mL) at room temperature over 20 min. After stirring the reaction mixture for 2 min, it was decomposed by addition of 2M HCl (5 mL). The solvent was removed under reduced pressure and the residue was diluted with ethyl ether (200 mL). The white precipitate formed was filtered and the filtrate was washed with saturated NaHCO$_3$ (2×15 mL) and brine (2×25 mL). The ethereal solution was dried over anhydrous MgSO$_4$ and the solvent was removed to afford 4.97 g of pure alcohol (24.6 mmol, 98.4% yield), mp 107°–108° C., $[\alpha]_D^{23}$ +41° (c, 2, MeOH). HPLC analysis (silica gel, THF:hexane 1:99) of the MPT ester indicated the e.e. to be 97% (97.65% e.e. corrected) [retention times: 11.92 min (major diastereomer) and 12.81 min (minor diastereomer)].

G. Reduction of 2-bromo-2-cyclohexen-1-one with 3 and BH$_3$.THF

To a solution of 3 (23.3 mg, 0.084 mmol) in 0.2 mL of THF and 0.06 ml of BH$_3$.THF (1.1M, 0.066 mmol) was added simultaneously a solution of 2-bromo-2-cyclohexen-1-one (147 mg, 0.84 mmol, 10 eq) in THF (1 mL) and BH$_3$.THF (0.396 mL, 0.435 mmol) over 15 min. After stirring the reaction mixture for 2 min, the mixture was decomposed by addition of 2M HCl (0.5 mL). The reaction mixture was diluted with ethyl ether (60 mL) and washed with saturated NaHCO$_3$ (2×15 mL) and brine (2×15 mL). Removal of the solvent after drying over anhydrous MgSO$_4$ afforded 174 mg of crude material. After chromatography (silica gel, 5% EtOAc/hexane) of the crude product, 126 mg of pure alcohol was obtained (0.711 mmol, 84.72% yield), $[\alpha]_D^{23}$ +73.05° (c 1.7, MeOH). The enantiomeric excess was determined by capillary GLC analysis of the MPT ester (170° C., methylsilicone column) to be 90.04% (91.05% corrected) [retention times: 7.12 min (major diastereomer) and 7.52 min (minor diastereomer)].

H. The results of a number of reductions using the process of the invention with (S)-5,5-diphenyl-2-methyl-3,4-propano-1,3,2-oxazaborolidine (3) as catalyst are shown in Table II.

TABLE II
Borane Reduction of Prochiral Ketones Catalyzed by 3

$$2\ R_S R_L CO + BH_3 \xrightarrow{3,\ THF} (R_S R_L CH-O)_2 BH \longrightarrow R_S R_L CHOH$$

| Prochiral Ketone | Equiv BH$_3$ | Equiv 3 | Reaction time (min) | temp (°C.) | Config. of Product$^a$ (% ee)$^b$ |
|---|---|---|---|---|---|
| C$_6$H$_5$COCH$_3$ | 0.6 | 0.1 | 2 | 34 | R(93.2) |
| C$_6$H$_5$COCH$_3$ | 0.6 | 0.1 | 2 | 23 | R(94.1) |
| C$_6$H$_5$COCH$_3$ | 0.6 | 0.1 | 2 | 10 | R(95.5) |
| C$_6$H$_5$COCH$_3$ | 0.6 | 0.1 | 2 | 2 | R(96.6)* |
| C$_6$H$_5$COCH$_3$ | 0.6 | 0.1 | 2 | −10 | R(94.5) |
| C$_6$H$_5$COCH$_3$ | 0.6$^c$ | 0.1 | 15 | 2 | R(95.5) |
| C$_6$H$_5$COC$_2$H$_5$ | 0.6 | 0.1 | 2 | −10 | R(96.7)* |
| C$_6$H$_5$COC$_2$H$_5$ | 0.6 | 0.05 | 2 | −10 | R(95.9) |
| C$_6$H$_5$COCH$_2$Cl | 0.6 | 0.1 | 2 | 32 | S(95.3)* |
| C$_6$H$_5$COCH$_2$Cl | 0.6 | 0.1 | 2 | 23 | S(94.9) |
| t-BuCOCH$_3$ | 0.6 | 0.1 | 2 | −10 | R(97.3) |
| α-tetralone | 0.6 | 0.1 | 2 | 23 | R(80.2) |
| α-tetralone | 0.6 | 0.1 | 2 | 2 | R(82.4) |
| α-tetralone | 0.6 | 0.1 | 2 | −10 | R(83.3) |
| α-tetralone | 0.6 | 0.25 | 2 | −10 | R(86.0)* |
| c-C$_6$H$_{11}$COCH$_3$ | 0.6 | 0.1 | 2 | −10 | R(83.8) |
| 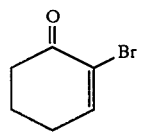 | 0.6 | 0.1 | 2$^d$ | 23 | R(91.0)$^e$ |
| 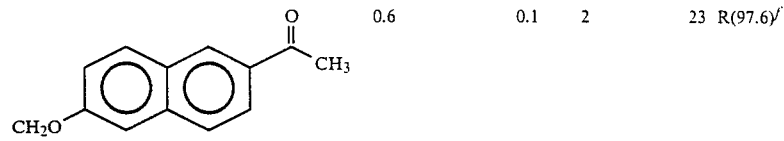 | 0.6 | 0.1 | 2 | 23 | R(97.6)$^f$ |

TABLE II-continued
Borane Reduction of Prochiral Ketones Catalyzed by 3

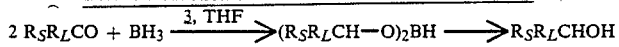

$$2\ R_SR_LCO + BH_3 \xrightarrow{3,\ THF} (R_SR_LCH\text{---}O)_2BH \longrightarrow R_SR_LCHOH$$

| Prochiral Ketone | Equiv BH$_3$ | Equiv 3 | Reaction time (min) | temp (°C.) | Config. of Product$^a$ (% ee)$^b$ |
|---|---|---|---|---|---|
| (structure with Ph-Ph-CoO, C$_5$H$_{11}$) | 0.6 | 0.1 | 2$^d$ | 23 | 15R:15S = 91:9$^g$ |
| 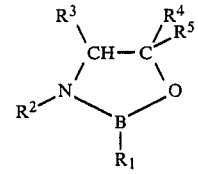 | 0.6 | 0.1 | 2$^d$ | 23 | S(68.5)$^h$ |

Notes:
$^a$For each entry, conversion of the prochiral ketone to the alcohol was >99.7%.
$^b$The absolute configuration was determined by isolation and measurement of rotation; the e.e. was determined by GLC analysis of the menthyloxycarbonyl derivative.
$^c$BH$_3$.(CH$_3$)$_2$S solution in toluene was used instead of BH$_3$.THF.
$^d$A solution of prochiral ketone and BH$_3$.THF was simultaneously added to the catalyst over 15 min.
$^e$The absolute configuration was based on mechanistic grounds. The e.e. was determined by capillary GLC analysis of the MPT ester.
$^f$The absolute configuration was based on mechanistic grounds. The e.e. was determined by HPLC analysis of the MPT ester.
$^g$The 15R:15S ratio was determined by HPLC analysis. Use of the (R)-enantiomer of catalyst 3 produced the 15S isomer of the alcohol in excess, with a 15S:15R ratio of 90:10.
$^h$The enantiomeric excess was determined by capillary GLC analysis of the MPT ester.
*Optimal conditions.

I. Reductions using other oxazaborolidines

Similar reductions with (S)-5,5-di(2-naphthyl)-3,4-propano-1,3,2-oxazaborolidine showed, in general, an even higher enantioselectivity than with the corresponding diphenyl compound (catalyst 2, part E of this Example). Also, reductions with (3S,2'R)-5,5-di(2-naphthyl)-2-(2'-(6-methoxy-2-naphthyl)propyl)-3,4-propano-1,3,2-oxazaborolidine showed a greater enantioselectivity than with the corresponding 2-methyl compound or the corresponding 2-methyl-5,5-diphenyl compound (catalyst 3, part G of this Example).

J. Reductions with the tricyclic oxazaborolidines derived from cis-2-azabicyclo[3.3.0]octan-8-one Reductions similar to those described in previous parts of this Example, using as catalysts the tricyclic oxazaborolidines derived from (1R,5S,8R)-2-aza-8-phenylbicyclo[3.3.0]octan-8-ol and its enantiomer and (1R,5S,8R)-2-aza-8-(2-naphthyl)bicyclo[3.3.0]octan-8-ol and its enantiomer with methyl-, n-butyl-, and (R)-2-(6-methoxy-2-naphthyl)propyl-boronic acid showed high enantioselectivity for a variety of reductions of prochiral ketones.

While it appears that the enantioselectivity of the reduction of any given prochiral ketone will vary with the catalyst, no one catalyst appears superior for the reduction of all ketones. However, one of ordinary skill in the art should have no difficulty, having regard to his own knowledge and this disclosure, in selecting a suitable catalyst, catalyst concentration, temperature, and other reaction conditions to achieve optimum enantioselectivity in the reduction of a chosen prochiral ketone.

I claim:

1. A chiral 1,3,2-oxazaborolidine of the formula:

$$\begin{array}{c} R^3 \quad\quad R^4 \\ \backslash \quad\quad /R^5 \\ CH\text{---}C \\ / \quad\quad \backslash \\ R^2\text{---}N \quad\quad O \\ \backslash \quad / \\ B \\ | \\ R_1 \end{array}$$

in which:

R$_1$ is lower alkyl or aralkyl;
R$_2$ is hydrogen, methyl, or ethyl;
R$_3$ is alkyl, aryl, or aralkyl; or R$_2$ and R$_3$, taken together with that part of the oxazaborolidine ring to which they are attached, form a 4-, 5-, or 6-membered ring, carbocyclic except for the oxazaborolidine nitrogen; and
R$_4$ and R$_5$ are independently alkyl, aryl, or aralkyl; or R$_2$ and R$_4$, taken together with that part of the oxazaborolidine ring to which they are attached, form a 5- or 6-membered ring, carbocyclic except for the oxazaborolidine nitrogen, and R$_5$ is hydrogen, or R$_2$, R$_3$, and R$_4$, taken together with that part of the oxazaborolidine ring to which they are attached, form two 5-membered ring, carbocyclic except for the oxazaborolidine nitrogen, cis-fused at the CH—R$_3$ bond.

2. A compound of claim 1 wherein R$^1$ is methyl.

3. A compound of claim 2 wherein R$_2$ and R$_3$, taken together with that part of the oxazaborolidine ring to which they are attached, form a 4-, 5-, or 6-membered ring, carbocyclic except for the oxazaborolidine nitrogen.

4. A compound of claim 3 wherein R$^4$ and R$^5$ are the same and are bulky alkyl, aryl, or aralkyl.

5. A compound of claim 4 wherein R$_2$ and R$_3$, taken together with that part of the oxazaborolidine ring to which they are attached, form a 5-membered ring, carbocyclic except for the oxazaborolidine nitrogen, and $R_4$ and $R_5$ are the same and are aryl.

6. The (S)-isomer of the compound of claim 5 wherein $R^2$ and $R^3$ form a 1,3-propano bridge and $R^4$ and $R^5$ are phenyl, namely (S)-5,5-diphenyl-2-methyl-3,4-propano-1,3,2-oxazaborolidine.

7. A compound of claim 2 wherein $R^2$ is hydrogen and $R^3$ is bulky alkyl, aryl, or aralkyl.

8. A compound of claim 7 wherein $R^4$ and $R^5$ are the same and are bulky alkyl, aryl, or aralkyl.

9. A compound of claim 8 wherein $R^3$ is bulky alkyl and $R^4$ and $R^5$ are the same and are aryl.

10. The (S)-isomer of the compound of claim 9 wherein $R^3$ is isopropyl and $R^4$ and $R^5$ are phenyl, namely (S)-5,5-diphenyl-2-methyl-4-(1-methylethyl)-1,3,2-oxazaborolidine.

11. A chiral 1,3,2-oxazaborolidine of the formula:

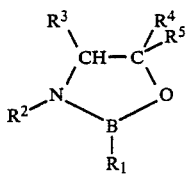

in which:

$R_1$ is hydrogen, lower alkyl, or aralkyl; and either:

(1) $R_2$ and $R_3$, taken together with that part of the oxazaborolidine ring to which they are attached, form a 4-, 5-, or 6-membered ring, carbocyclic except for the oxazaborolidine nitrogen; and $R_4$ and $R_5$ are independently alkyl, aryl, or aralkyl, or (2) $R_2$ and $R_4$, taken together with that part of the oxazaborolidine ring to which they are attached, form a 5- or 6-membered ring, carbocyclic except for the oxazaborolidine nitrogen; $R_3$ is alkyl, aryl, or aralkyl; and $R_5$ is hydrogen, or (3) $R_2$, $R_3$, and $R_4$, taken together with that part of the oxazaborolidine ring to which they are attached, form two 5-membered rings, carbocyclic except for the oxazaborolidine nitrogen, cis-fused at the CH—$R_3$ bond; and $R_5$ is alkyl, aryl, or aralkyl.

12. A compound of claim 11 wherein $R^1$ is hydrogen.

13. A compound of claim 12 wherein $R_2$ and $R_3$, taken together with that part of the oxazaborolidine ring to which they are attached, form a 4-, 5-, or 6-membered ring, carbocyclic except for the oxazaborolidine nitrogen.

14. A compound of claim 13 wherein $R^4$ and $R^5$ are the same and are bulky alkyl, aryl, or aralkyl.

15. A compound of claim 14 wherein $R_2$ and $R_3$, taken together with that part of the oxazaborolidine ring to which they are attached, form a 4-membered ring, carbocyclic except for the oxazaborolidine nitrogen, and $R_4$ and $R_5$ are the same and are bulky alkyl.

16. A compound of claim 14 wherein $R_2$ and $R_3$, taken together with that part of the oxazaborolidine ring to which they are attached, form a 4-membered ring, carbocyclic except for the oxazaborolidine nitrogen, and $R_4$ and $R_5$ are the same and are aryl.

17. The (S)-isomer of the compound of claim 16 wherein $R^2$ and $R^3$ form a 1,2-ethano bridge and $R^4$ and $R^5$ are phenyl, namely (S)-3,4-ethano-5,5-diphenyl-1,3,2-oxazaborolidine.

18. A compound of claim 14 wherein $R_2$ and $R_3$, taken together with that part of the oxazaborolidine ring to which they are attached, form a 5-membered ring, carbocyclic except for the oxazaborolidine nitrogen, and $R_4$ and $R_5$ are the same and are bulky alkyl.

19. A compound of claim 14 wherein $R_2$ and $R_3$, taken together with that part of the oxazaborolidine ring to which they are attached, form a 5-membered ring, carbocyclic except for the oxazaborolidine nitrogen, and $R_4$ and $R_5$ are the same and are aryl.

20. The (S)-isomer of the compound of claim 19 wherein $R^2$ and $R^3$ form a 1,3-propano bridge and $R^4$ and $R^5$ are phenyl, namely (S)-5,5-diphenyl-3,4-propano-1,3,2-oxazaborolidine.

21. A chiral tetrahydro-1,3,2-oxazaborine of the formula:

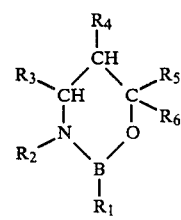

in which:

$R_1$ is hydrogen, lower alkyl, or aralkyl;

$R_2$ is hydrogen, methyl, or ethyl;

$R_3$ is alkyl, aryl, or aralkyl; or $R_2$ and $R_3$, taken together with that part of the oxazaborine ring to which they are attached, form a 4-, 5-, or 6-membered ring, carbocyclic except for the oxazaborine nitrogen;

$R_4$ is hydrogen, alkyl, or aryl; or $R_2$ and $R_4$, taken together with that part of the oxazaborine ring to which they are attached, form a 5- or 6-membered ring, carbocyclic except for the oxazaborine nitrogen; and $R_5$ and $R_6$ are independently alkyl, aryl, or aralkyl; or $R_2$ and $R_5$, taken together with that part of the oxazaborine ring to which they are attached, form a 6-membered ring, carbocyclic except for the oxazaborine nitrogen, and $R_6$ is hydrogen.

22. A compound of claim 21 wherein $R^1$ is hydrogen.

23. A compound of claim 22 wherein $R_2$ and $R_3$, taken together with that part of the oxazaborine ring to which they are attached, form a 4-, 5-, or 6-membered ring, carbocyclic except for the oxazaborine nitrogen.

24. A compound of claim 23 wherein $R^4$ is hydrogen.

25. A compound of claim 24 wherein $R^5$ and $R^6$ are the same and are bulky alkyl, aryl, or aralkyl.

26. A compound of claim 25 wherein $R_2$ and $R_3$, taken together with that part of the oxazaborine ring to which they are attached, form a 5-membered ring, carbocyclic except for the oxazaborine nitrogen, and $R_5$ and $R_6$ are the same and are aryl.

27. A compound of claim 21 wherein $R^1$ is methyl and $R^4$ is hydrogen.

28. A compound of claim 27 wherein $R_2$ and $R_3$, taken together with that part of the oxazaborine ring to which they are attached, form a 4-, 5-, or 6-membered ring, carbocyclic except for the oxazaborine nitrogen.

29. A compound of claim 28 wherein $R^5$ and $R^6$ are the same and are bulky alkyl, aryl, or aralkyl.

30. A compound of claim 29 wherein $R_2$ and $R_3$, taken together with that part of the oxazaborine ring to which they are attached, form a 5-membered ring, carbocyclic except for the oxazaborine nitrogen, and $R_5$ and $R_6$ are the same and are aryl.

* * * * *